United States Patent
Ward

(10) Patent No.: US 8,012,100 B2
(45) Date of Patent: Sep. 6, 2011

(54) FLUID PRESSURE-ACTUATED MEDICAL DEVICE

(75) Inventor: Tim E. Ward, Springville, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2038 days.

(21) Appl. No.: 10/262,138

(22) Filed: Oct. 1, 2002

(65) Prior Publication Data

US 2004/0064067 A1   Apr. 1, 2004

(51) Int. Cl.
*A61B 10/00*   (2006.01)

(52) U.S. Cl. ........................................ 600/562

(58) Field of Classification Search .................. 600/562, 600/564, 565, 567; 606/113, 114, 41
See application file for complete search history.

(56) References Cited

U.S. PATENT DOCUMENTS

| | | | |
|---|---|---|---|
| 3,363,833 A | 1/1968 | Laerdal | |
| 5,271,379 A | 12/1993 | Phan et al. | |
| 5,312,416 A * | 5/1994 | Spaeth et al. | 606/114 |
| 5,337,754 A * | 8/1994 | Heaven et al. | 600/562 |
| 5,409,012 A * | 4/1995 | Sahatjian | 600/562 |
| 5,527,280 A * | 6/1996 | Goelz | 604/99.02 |
| 5,593,412 A * | 1/1997 | Martinez et al. | 623/1.11 |
| 5,944,728 A | 8/1999 | Bates | |
| 6,096,053 A | 8/2000 | Bates | |
| 6,142,993 A * | 11/2000 | Whayne et al. | 606/41 |
| 6,273,861 B1 * | 8/2001 | Bates et al. | 600/567 |
| 6,319,262 B1 | 11/2001 | Bates et al. | |
| 6,348,056 B1 | 2/2002 | Bates et al. | |
| 6,383,196 B1 | 5/2002 | Leslie et al. | |
| 6,491,698 B1 | 12/2002 | Bates et al. | |
| 6,506,201 B2 * | 1/2003 | Di Caprio et al. | 606/192 |
| 2001/0049535 A1 | 12/2001 | Leveillee | |

FOREIGN PATENT DOCUMENTS

| | | |
|---|---|---|
| DE | 3400416 | 7/1985 |
| DE | 9207414 | 8/1992 |
| EP | 0974321 | 1/2000 |

OTHER PUBLICATIONS

PCT International Search Report of PCT/US 03/30989.

* cited by examiner

*Primary Examiner* — Max Hindenburg
*Assistant Examiner* — Fangemonique Smith
(74) *Attorney, Agent, or Firm* — Finnegan, Henderson, Farabow, Garrett & Dunner LLP

(57) ABSTRACT

An apparatus and method are described for actuating a minimally invasive medical device using fluid pressure. The invention involves a medical device that includes a fluid source, such as a compressible bladder that may apply positive fluid pressure into a sheath to controllably deploy an end-effector from a distal end of the sheath. In some embodiments, the fluid source may apply negative fluid pressure into the sheath to controllably retract the end-effector into the distal end of the sheath. Typical end-effectors for use with the medical device of the invention include biopsy devices and retrieval devices, including basket-type retrieval devices and grasper retrieval devices. Generally, the fluid that is used to actuate the device may be a liquid or a gas, including air.

42 Claims, 5 Drawing Sheets

FLUID PRESSURE-ACTUATED MEDICAL DEVICE

TECHNICAL FIELD

The invention generally relates to a minimally invasive medical device for use in procedures such as retrieval or biopsy. More particularly, the invention relates to a minimally invasive medical device that is actuated through application of fluid or air pressure.

BACKGROUND

Current minimally invasive medical devices for use in operations such as retrieval or biopsy are typically operated by mechanical means, using a pull wire. Typically, a distal end of the pull wire connects to an end-effector, such as a basket-type retrieval device, a grasper, a biopsy device, etc. Generally, the proximal end of the pull wire is connected to a control or actuation mechanism in the handle of the medical device.

The pull wire typically transmits movement in a control or actuation mechanism in the handle of the device to the end-effector. Through use of such a pull wire, or a series of pull wires, the end-effector can be controlled to extend from the end of a sheath, retract into the sheath, cut away a sample for a biopsy, or to take other actions that are typically performed by devices such as graspers, basket-type retrieval devices or biopsy devices.

The pull wire in these devices is typically made of metal, and is often somewhat rigid. This rigidity can make it more difficult to maneuver the medical device within the body.

Additionally, use of a pull wire and actuation mechanisms associated with the pull wire add substantially to the number of component parts of a minimally invasive medical device. This increases the cost and complexity of the device, and increases the chance of failure of the device.

Minimally invasive medical devices that use actuation means other than a pull wire have been developed. For example, some devices use compressed gas to propel a needle, biopsy device, or other medical device. Such pneumatically-actuated medical devices typically use a "firing trigger" mechanism to trigger the release of the compressed gas. Such mechanisms provide very little control, and are typically only able to perform the single action of rapidly propelling a device such as a needle.

While this lack of control may be acceptable for some procedures, many medical procedures require fine control over the rate, timing, and precise positioning of a device. Other applications for minimally invasive medical devices require more varied action than simply propelling a portion of the device forward. For example, many procedures require a medical device that can be controllably extended and retracted. Devices that use compressed gas and "firing triggers" typically do not provide such fine control or varied actions.

SUMMARY OF THE INVENTION

In view of the foregoing, a minimally invasive medical device that provides a high degree of controllability, but does not use pull wires or other actuation mechanisms that may substantially reduce the flexibility of the device is desirable. The present invention, in one embodiment, provides a minimally invasive medical device in which an end-effector, such as a retrieval device or biopsy device, may be extended or retracted through controlled use of fluid pressure. Because no pull wire is needed to control the device, a medical device in accordance with this embodiment of the invention provides increased flexibility relative to known devices that perform similar operations. Additionally, medical devices constructed in accordance with this embodiment of the invention require fewer parts than other devices that perform similar functions, thereby decreasing manufacturing costs and increasing reliability.

In one aspect, the invention provides a medical device that includes a sheath, and an operator-controlled fluid source adapted to apply positive fluid pressure into the sheath to deploy at least a portion of an end-effector from a distal end of the sheath in a controlled fashion. In some embodiments, the fluid source is adapted to apply negative fluid pressure into the sheath to controllably retract at least a portion of the end-effector into the sheath. Typical end-effectors for use with the medical device of the invention include biopsy devices and retrieval devices, including basket-type retrieval devices and grasper retrieval devices, and the like. In one embodiment, the fluid that is used to actuate the device may be a liquid. In another embodiment, the actuating fluid is a gas, such as air. In another embodiment, the actuating fluid is a gel. According to other embodiments, any suitable actuating fluid may be employed.

In some embodiments, the end-effector includes a first hub, disposed within the sheath in a manner that permits it to slide within the sheath. According to one feature, the first hub is adapted to substantially form a seal with the sheath. Applying a positive fluid pressure within the sheath causes the first hub to move in a distal direction within the sheath. In some embodiments, applying a negative fluid pressure within the sheath causes the first hub to move in a proximal direction within the sheath. With the end-effector connected to the first hub, this movement of the hub causes the end-effector to be moved from a "closed" position within the sheath, to an "open" position, in which a portion of the end-effector extends from the distal end of the sheath.

In some embodiments, a stop, located within the sheath, prevents the first hub from moving in a distal direction past the stop. Some embodiments, particularly those in which a negative fluid pressure may be applied, also include a second stop that prevents the hub from moving in a proximal direction past the second stop.

In some embodiments, the operator-controlled fluid source is a bladder that is in fluid communication with the sheath. When pressure is applied to the bladder, the bladder pushes fluid into the sheath, thereby applying positive fluid pressure. When pressure is released from the bladder, the bladder pulls fluid from the sheath, applying negative fluid pressure.

In one embodiment, the bladder is placed on a handle that is located at a proximal end of the sheath. In some embodiments, the bladder may be placed at a location on the handle that permits an operator to operate the bladder using his or her thumb. According to one feature, the handle and bladder have an ergonomic design, which provides easy and comfortable operation of the medical device.

In some embodiments, an elastic member, such as a spring is used to retract the end-effector. In some such embodiments, the elastic member is compressed when the end-effector is deployed, while in other embodiments, the elastic member is stretched when the end-effector is deployed. In these embodiments, the elastic member retracts at least a portion of the end-effector into the sheath when the positive fluid pressure is insufficient to overcome the force applied by the stretched or compressed elastic member.

Some devices for use with the medical device of the invention may require actuation of more than one portion of the device. For example, in some biopsy devices, multiple steps may be used to take a sample. In one such biopsy device, a stylet is extended from the distal end of a sheath. Once the stylet is fully extended, a cannula is extended over the stylet to capture a tissue sample. In one embodiment, the invention provides a mechanism for controlling or actuating such devices by using multiple slidable hubs. In an alternative embodiment, the invention employs an elastic member, such as a spring, and a latch for control and actuation.

In some embodiments, the end-effector includes a second hub that is disposed within the sheath at a position distal of the stop, and that is able to slide within the sheath. In some embodiments, a second stop disposed within the sheath prevents the second hub from moving in a distal direction past the second stop.

In some embodiments, the first hub includes an opening that permits a limited flow of fluid through the first hub. When the first hub is prevented from further distal movement by the first stop, this opening permits fluid pressure to move the second hub in a distal direction.

In some such embodiments, the end-effector comprises a biopsy device, the first hub is connected to a stylet portion of the biopsy device, and the second hub is connected to a cannula portion of the biopsy device. When the first hub is moved in a distal direction, the stylet portion of the biopsy device is extended from the distal end of the sheath. When the second hub is moved in a distal direction, the cannula portion of the biopsy device is extended from the distal end of the sheath.

In some embodiments, a notch is formed in the stylet portion of the biopsy device, and the cannula portion of the biopsy device has a sharp edge. When the cannula portion of the biopsy device is extended from the distal end of the sheath, the cannula portion of the biopsy device slides over the stylet portion of the biopsy device. This permits the cannula to cut tissue, and to capture a tissue sample within the notch formed in the stylet portion of the biopsy device.

Instead of using two (or more) sliding hubs to control end-effectors with multiple moving portions, elastic members and latches may be used. In some embodiments, the end-effector includes a first portion, connected to the first hub, and a second portion. A proximal end of an elastic member, such as a spring, connects to the first hub, and a distal end of the elastic member connects to the second portion of the end-effector. Additionally, the medical device includes a latch that holds the second portion of the end-effector in a stationary position relative to the sheath until the latch is released.

In one embodiment, the elastic member compresses when the first hub moves in a distal direction. In some embodiments, the elastic member propels the second portion of the end-effector in a distal direction when the latch is released.

For example, if the end-effector is a biopsy device, the first portion of the end-effector may be a stylet, and the second portion may be a cannula. When positive fluid pressure is applied, the stylet extends from the distal end of the sheath, and the elastic member compresses. When the latch is released, the cannula is propelled in a distal direction by the elastic member, extending from the distal end of the sheath, and sliding over the stylet, capturing a tissue sample in a notch formed in the stylet.

In another aspect, the invention provides a method for controlling an end-effector, in which positive fluid pressure is applied to controllably deploy the end-effector from the distal end of a sheath. In some embodiments, applying positive fluid pressure is accomplished by applying pressure to a bladder in fluid communication with the sheath. Some embodiments use negative fluid pressure to controllably retract the end-effector into the sheath. In one embodiment, releasing pressure from a bladder in fluid communication with the sheath applies negative fluid pressure.

These and other objects, advantages, and features of the invention will become apparent through reference to the following description, the accompanying drawings, and the claims. Furthermore, it will be understood that the features of the various embodiments described herein are not mutually exclusive, and can exist in various combinations and permutations.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

Figure 1:
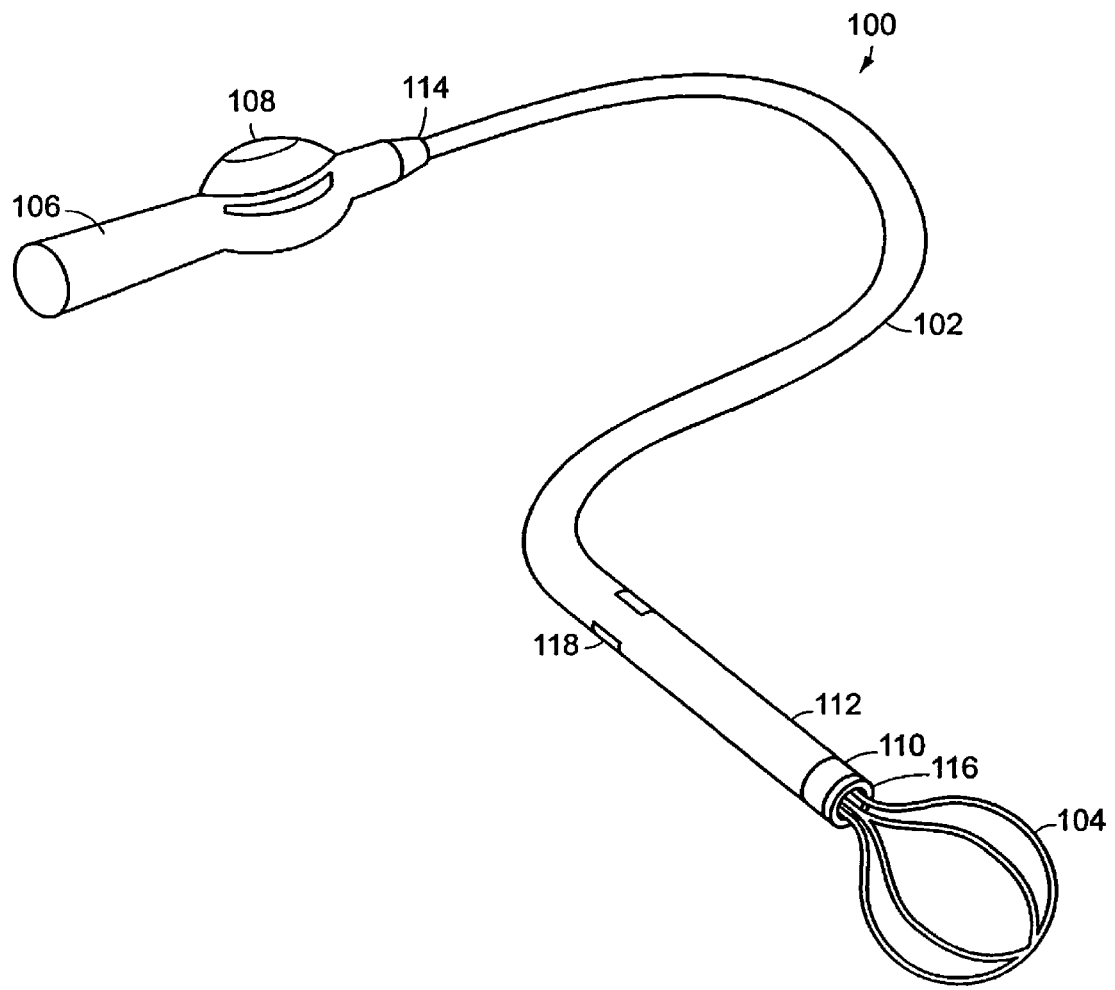
FIG. 1 shows an illustrative embodiment of a medical device in accordance with the invention.

FIG. 1 shows a view of a medical device 100 in accordance with an illustrative embodiment of the present invention. The medical retrieval device 100 includes a sheath 102, an end-effector 104 (in this case, a basket-type retrieval device), disposed at a distal end 112 of the sheath 102, and a handle 106, disposed at a proximal end 114 of the sheath 102.

The handle 106 includes a bladder 108, which is connected through the handle 106 to the sheath 102 so that it is in fluid communication with the sheath 102. The bladder 108 and the sheath 102 are filled with a fluid, such as air, water, a saline solution, or other liquids, gels, or gasses.

The end-effector 104 is connected to an inner hub 110, which is disposed within the sheath 102 in a manner that permits it to slide between a proximal stop 118 and a distal stop 116. Preferably, a substantially effective seal is created between the inner hub 110 and the sheath 102, inhibiting the escape of fluid from sheath the 102 past the inner hub 110.

Pressure applied to the bladder 108 forces fluid out of the bladder 108, and into the sheath 102, causing positive fluid or air pressure in the sheath 102, and pushing the inner hub 110 towards the distal end 112 of the sheath 102. This extends the end-effector 104, which is connected to the inner hub 110, into an "open" position, thereby deploying the end-effector 104. The movement of the inner hub 110 is limited by the distal stop 116, which prevents the inner hub 110 from sliding distally any farther than the distal stop 116.

Releasing pressure from the bladder 108, fluid in the sheath 102 draws back into the bladder 108, causing negative fluid pressure in the sheath 102. This negative pressure pulls the inner hub 110 and the end-effector 104 towards the proximal end 114 of the sheath 102, retracting the end-effector 104 into a "closed" position within the sheath 102. The proximal movement of the inner hub 110 is limited by the proximal stop 118, which prevents the inner hub 110 from sliding proximally farther than the proximal stop 118.

In FIG. 1, the medical device is shown with the end-effector 104 fully extended, and the inner hub 110 abutting the distal stop 116. This is the configuration that the medical device would have if sufficient pressure were applied to the bladder 108 to completely extend the end-effector 104.

The sheath 102, the end-effector 104, the handle 106, the bladder 108, the inner hub 110, the proximal stop 118, and the distal stop 116 as illustrated in FIG. 1 are not necessarily shown in their correct size or proportion to each other. Preferably, the sheath 102 is dimensioned to fit the requirements of its application in the body. For example, for urological applications, the outside diameter of the sheath 102 is typically between 1.7 and 8.0 french, though some applications may call for larger or smaller sizes.

The handle 106 is preferably sized to fit easily in an operator's hand, and the bladder 108 is preferably sized and placed on the handle 106 in a position that permits an operator to use his or her thumb to depress the bladder 108. In preferred embodiments of the invention, the handle 106 and the bladder 108 are ergonomically sized and placed, providing a medical device that is comfortable and easy to use. However, other sizes and shapes for the handle 106 are within the scope of the invention. Additionally, excluding the handle 106 from the device entirely, so that the bladder 108 is directly connected to the sheath 102 is within the scope of the invention. Similarly, alternative placements of the bladder 108, including separating the bladder 108 from the handle 106 are also within the scope of the invention.

Advantageously, since the end-effector 104 of the medical device 100 is operated using fluid pressure, there is no need for a pull wire to be used to operate the end-effector 104. Since there is no pull wire, the flexibility of the medical device 100 is increased. Additionally, fewer mechanical components are needed to construct the medical device 100, potentially decreasing the manufacturing cost and likelihood of failure of the medical device 100.

A high degree of control is achieved by use of an operator-controlled fluid source, such as the bladder 108. For example, in some embodiments, by compressing the bladder 108 to varying degrees, an operator may determine the degree to which the end-effector 104 extends from the distal end of the sheath 102. In some embodiments, by releasing pressure from the bladder 108, the operator may retract the end-effector 104 into the sheath 102. In various embodiments, an operator-controlled fluid source, such as the bladder 108, can control the rate or speed of deployment, the degree of deployment, the position, or other operational aspects of the medical device 100 and end-effector 104.

Figure 2A:
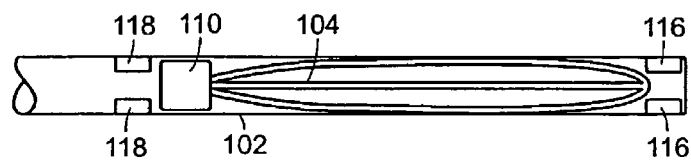
FIGS. 2A-B show an embodiment of a retrieval end-effector for use with a medical device in accordance with the invention.
Figure 2B:
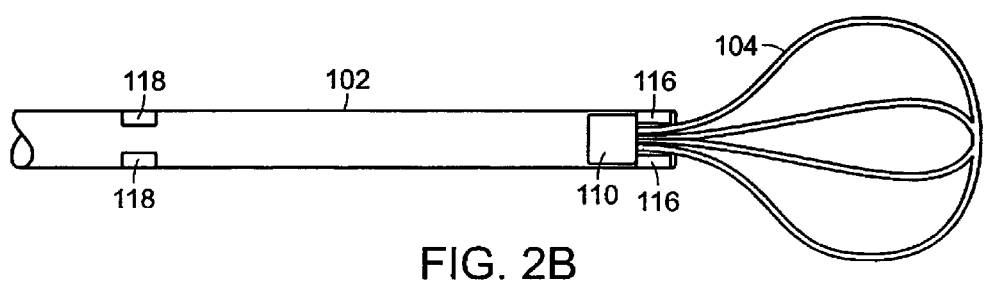

FIGS. 2A and 2B show an embodiment of the invention in a closed and an open position, respectively. In FIG. 2A, the end-effector 104 is in the closed position, collapsed within the sheath 102. As can be seen, the inner hub 110 is positioned near the proximal stop 118. As shown in FIG. 2B, applying positive fluid pressure within the sheath 102 pushes the inner hub 110 into a position adjacent to the distal stop 116, and pushes the end-effector 104 out of the end of the sheath 102, into an open position. In the illustrative embodiment shown in FIGS. 2A and 2B, the end-effector is a basket-type retrieval device, which expands into the form shown in FIG. 2B when extended out of the distal end of the sheath 102.

Figure 3A:
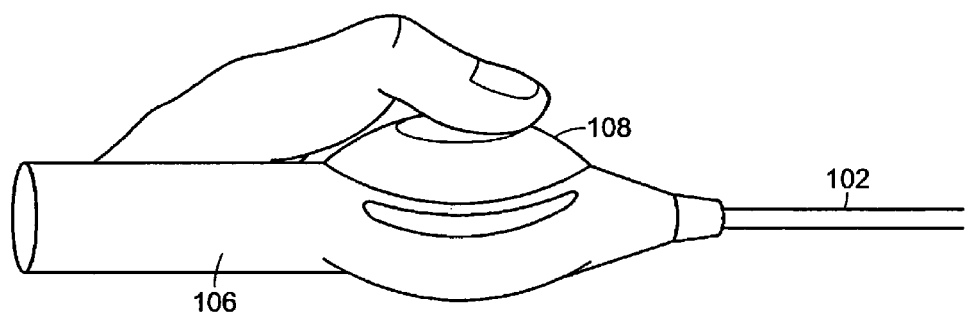
FIGS. 3A-B illustrate the operation of an embodiment of a medical device in accordance with the invention.
Figure 3B:
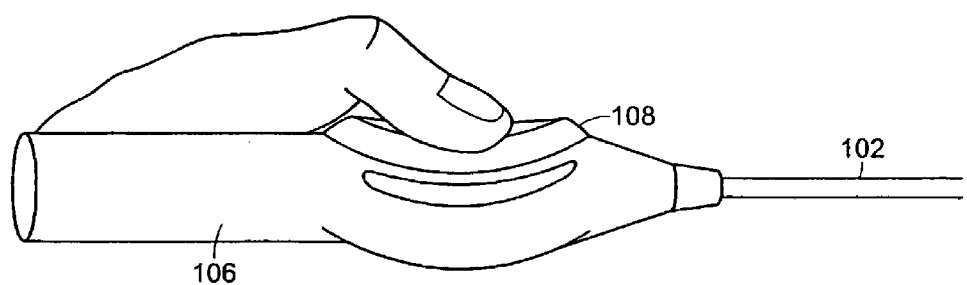

FIGS. 3A and 3B illustrate the operation of an embodiment of the medical device of the invention. In FIG. 3A, an operator applies no pressure to the bladder 108, so the end-effector (not shown) remains in the closed position, collapsed within the sheath 102. In FIG. 3B, the operator depresses the bladder 108, forcing fluid from the bladder 108 into the sheath 102, causing positive fluid pressure in the sheath 102. This positive pressure pushes the end-effector out of the distal end of the sheath 102, into its open position. The operator may return the end-effector to the closed position by ceasing the application of pressure on the bladder 108. This causes negative fluid pressure in the sheath 102, which pulls the end-effector back into the closed position. The operator can extend the end-effector out of the distal end of the sheath 102 to varying degrees by varying the amount of pressure applied to the bladder 108.

Figure 4A:
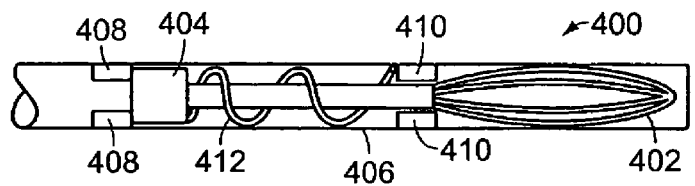
FIGS. 4A-B show an embodiment of a retrieval end-effector for use with a medical device in accordance with the invention.
Figure 4B:
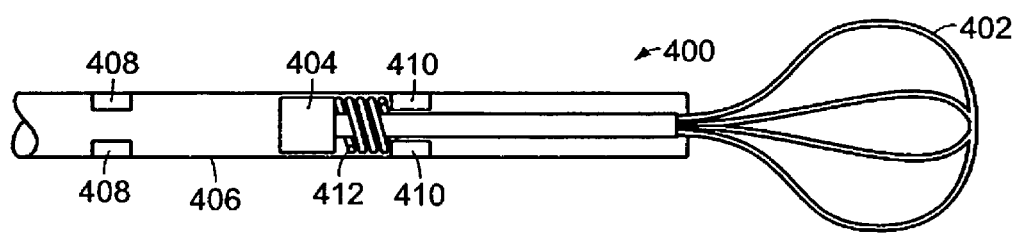

Referring now to FIGS. 4A-4B, another embodiment of the medical device of the invention is shown. In FIG. 4A, a medical device 400, of which only a distal portion is shown, is in its closed position. As in previous embodiments, an end-effector 402 (a basket-type retrieval device, in this embodiment) connects to an internal hub 404. The internal hub 404 slides within a sheath 406, and preferably forms a seal with the sheath 406. A proximal stop 408 and a distal stop 410 limit the range of movement of the internal hub 404. As in previously discussed embodiments, application of positive fluid pressure pushes the internal hub 404 and the end-effector 402 in a distal direction, extending the end-effector 402 into its open position.

The medical device 400 includes an elastic member, such as a spring 412, which provides a positive closure mechanism for the medical device 400. When the medical device 400 is in the closed position, with the end-effector 402 collapsed within the sheath 406, and the internal hub 404 adjacent to the proximal stop 408, the spring 412 is in an equilibrium position, and does not exert force on the internal hub 406.

As shown in FIG. 4B, when sufficient fluid pressure pushes the inner hub 404 towards the distal stop 410, the end-effector 402 extends from the sheath 406, into its open position. In the open position, the spring 412 is compressed, and exerts a force on the internal hub 404 to push the internal hub 404 towards the proximal stop 408. The force exerted by the spring 412 assists in placing the medical device 400 into the closed position when the fluid pressure is released or becomes insufficient to compress the spring 412.

Other elastic members, such as elastic materials may be used in place of the spring 412. Additionally, instead of compressing the elastic member, in some embodiments, extending the end-effector stretches the elastic member. When the elastic member is stretched in this manner, it exerts a force to assist in retracting the end-effector.

As mentioned above, numerous types of end-effectors may be used in conjunction with the fluid pressure-actuated medical device of the present invention. For example, instead of using a basket-type retrieval device as the end-effector, a grasper retrieval device, cutting device or any other device previously deployed using a pull wire may be used.

Figure 5:
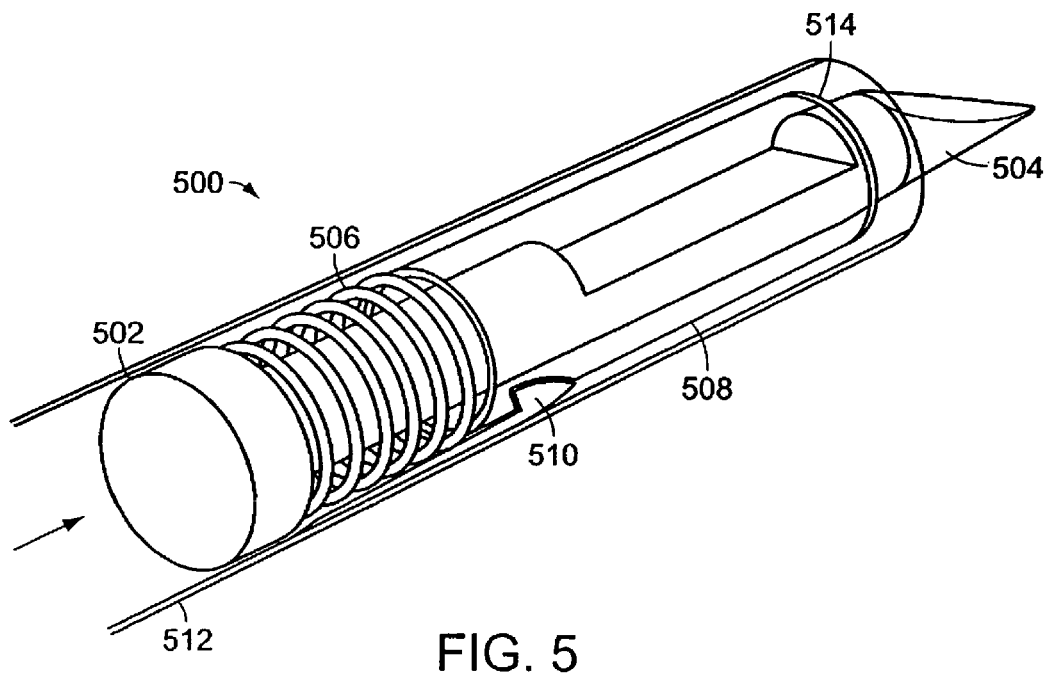
FIG. 5 shows an embodiment of a biopsy end-effector for use with a medical device in accordance with the invention.

FIG. 5 shows a biopsy device end-effector for use with an embodiment of a medical device in accordance with the principles of the invention. A biopsy device 500 includes a hub 502, to which a stylet 504 is rigidly attached. An elastic member, such as a spring 506 surrounds a proximal portion of the stylet 504, and connects at its proximal end to the hub 502, and at its distal end to a cannula 508.

A latch 510, which is preferably connected to a sheath 512, holds the cannula 508 in place. The latch 510 holds the cannula 508 at a fixed position within the sheath 512, while permitting the hub 502 and the stylet 504 to be pushed forward by fluid pressure. As the fluid pressure pushes the hub 502 forward, the stylet 504 extends out of the distal end of the sheath 512, and the cannula 508 remains stationary, causing the spring 506 to compress. When the stylet 504 fully extends, the hub 502 causes the latch 510 to release, propelling the cannula 508 forward, to enclose the stylet 504. The cannula 508 includes a sharp edge 514, that cuts tissue when propelled forward, capturing a sample of the tissue within a notch formed in the stylet 504.

The biopsy device 500 fits within the sheath 512. Preferably, the hub 502 forms a substantially effective seal with the sheath 512 so that it can be propelled forward by positive fluid or air pressure in the sheath 512. In the embodiment shown in FIG. 5, the latch 510 acts as a stop, preventing the hub 502 from being propelled past the latch 510. In other embodiments, stops (not shown), such as the proximal and distal stops shown in previously embodiments may be used.

Figure 6A:
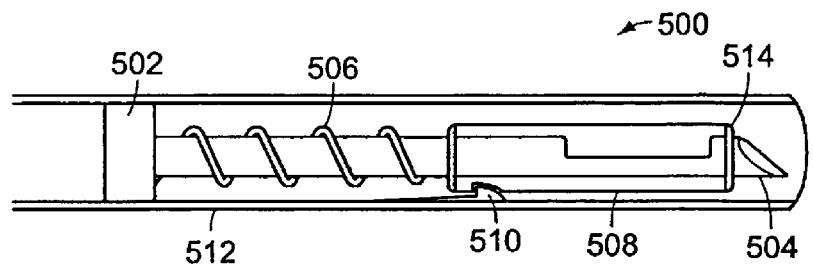
FIGS. 6A-C illustrate operation of the biopsy end-effector of FIG. 5.
Figure 6B:
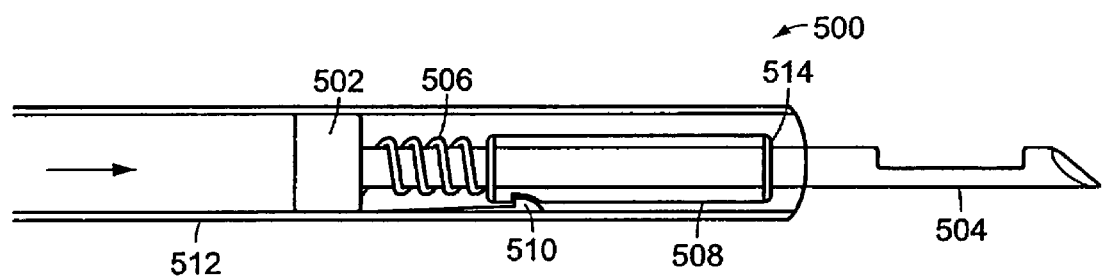
Figure 6C:
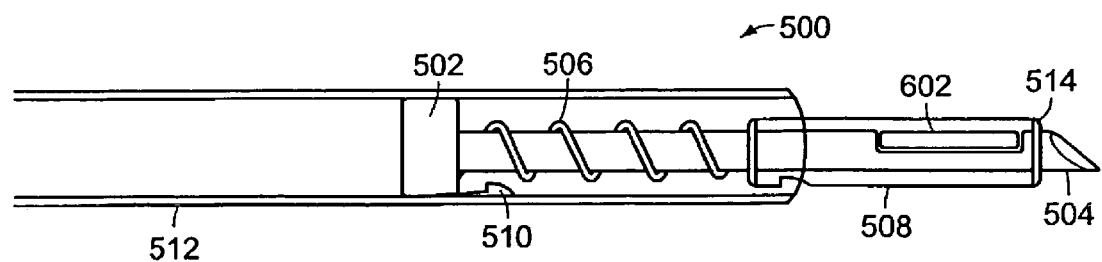

FIGS. 6A-6C show the operation of the biopsy device 500. In FIG. 6A, the biopsy device 500 is within the sheath 512, with the spring 506 in an equilibrium position, and the cannula 508 held in place by the latch 510.

In FIG. 6B, an operator has started to apply pressure to a fluid filled bladder (not shown) in fluid communication with the sheath 512, causing positive fluid pressure within the sheath 512 to propel the hub 502 towards the distal end of the sheath 512, thereby extending the stylet 504. Because the hub 502 is being pushed towards the distal end of the sheath 512, and the cannula 508 is being held in place, the spring 506 compresses. In FIG. 6B, the hub 502 has not yet caused the latch 510 to release the cannula 508.

In FIG. 6C, the latch 510 has been released, causing the spring 506, which was compressed, to propel the cannula 508 forward over the stylet 504. When the cannula 508 is propelled forward, it cuts tissue, capturing a tissue sample 602 within a slot formed in the stylet 504.

Figure 7:
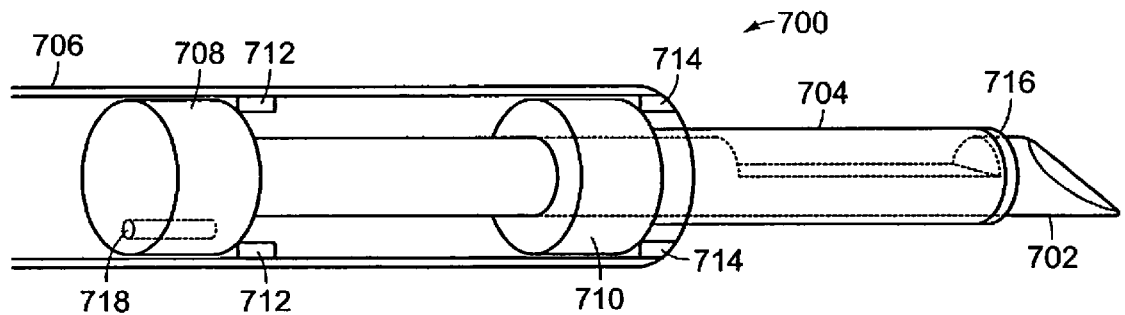
FIG. 7 shows an embodiment of a biopsy end-effector for use with a medical device in accordance with the invention.

FIG. 7 shows another embodiment of a biopsy device for use as an end-effector in a medical device according to the invention. In the embodiment shown in FIG. 7, no spring is needed to propel the cannula forward to cut tissue, as in the previous embodiment. Instead, fluid pressure is used to propel both the stylet and the cannula.

In FIG. 7, a biopsy device 700 is shown in a fully extended position, with a stylet 702 and a cannula 704 fully extended from the distal end of a sheath 706. The stylet 702 attaches to a stylet hub 708, and the cannula 704 attaches to a cannula hub 710. Preferably, the stylet hub 708 and the cannula hub 710 form seals with the sheath 706.

A stylet stop 712 limits the distal movement of the stylet hub 708 (and, therefore, of the stylet 702). The stylet stop 712 prevents the stylet hub 708 from advancing in a distal direction past the stylet stop 712. Note that the stylet stop 712 may also prevent the cannula hub 710 from moving in a proximal direction past the stylet stop 712. Optionally, an additional proximal stop (not shown) may be included to limit the proximal movement of the stylet hub 708.

A cannula stop 714 limits the distal movement of the cannula hub 710 (and the cannula 704). The cannula stop 714, which may be integrated into a distal tip of the sheath 706, prevents the cannula hub 710 from advancing in a distal direction past the cannula stop 714. As noted above, the stylet stop 712 may limit the proximal movement of the cannula hub 710.

The stylet hub 708 includes a small hole 718 which permits a limited amount of fluid to pass through the stylet hub 708 into the area between the stylet hub 708 and the cannula hub 710. In operation, positive fluid pressure first pushes the stylet hub 708 in a distal direction, extending the stylet 702 from the distal end of the sheath 706. When the stylet 702 is fully extended, the stylet stop 708 prevents further distal movement of the stylet hub 708.

At this point, fluid forced through the hole 718 in the stylet hub 708 causes positive fluid pressure to push the cannula hub 710 (and the cannula 704) in a distal direction, extending the cannula 704 out of the distal end of the sheath 706. As the cannula 704 extends over the stylet 702, a sharp edge 716 of the cannula 704 cuts tissue, capturing a tissue sample within a notch formed in the stylet 702. When the cannula 704 is fully extended, the cannula stop 714 prevents further distal movement of the cannula hub 710.

Figure 8A:
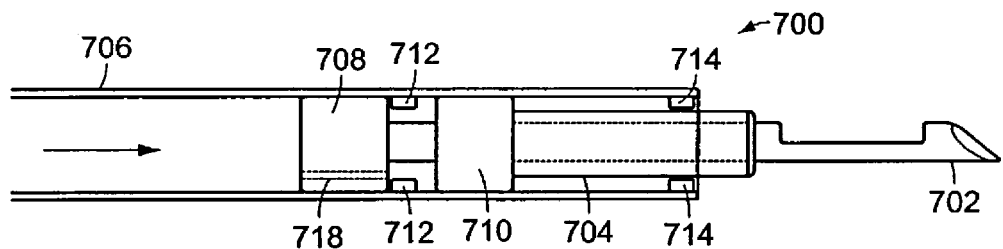
FIGS. 8A-B illustrate the operation of the biopsy end-effector of FIG. 7.
Figure 8B:
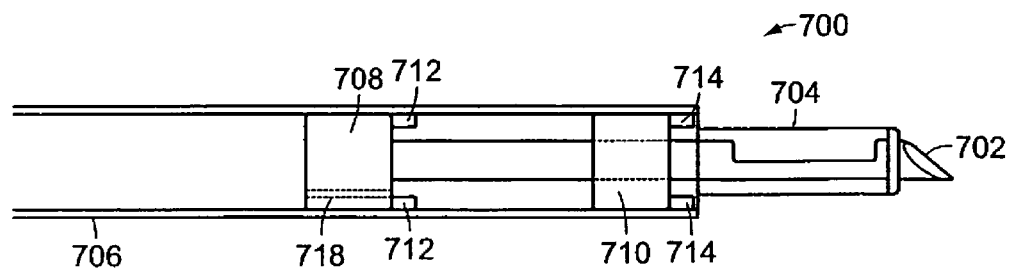

FIGS. 8A-B illustrate this process. In FIG. 8A, positive fluid pressure has propelled the stylet 702 out of the distal end of the sheath 706. The stylet stop 712 is preventing the stylet hub 708 from further movement in a distal direction. The cannula hub 714 has not yet been pushed in a distal direction by a substantial amount, and the cannula 704 is still within the sheath 706.

In FIG. 8B, when the stylet hub 708 is prevented from further distal movement by the stylet stop 712, fluid forced through the hole 718 in the stylet hub 708 propels the cannula 704 out of the distal end of the sheath 706. In FIG. 8B, the cannula 704 is fully extended, and further distal movement of the cannula hub 710 is prevented by the cannula stop 714.

In some embodiments, the biopsy end-effectors described with reference to FIGS. 5-8 may be retracted by application of negative fluid pressure. In other embodiments, the end-effectors of FIGS. 5-8 may not require retraction. In addition, such biopsy devices may be operated through application of short bursts of fluid pressure, rather than through substantially continuous application of pressure to a fluid filled bladder in fluid communication with a sheath.

Other embodiments incorporating the concepts disclosed herein are within the spirit and scope of the invention. The described embodiments are illustrative of the invention and not restrictive.

What is claimed is:

1. A medical device comprising:
   a sheath having proximal and distal ends, and an operator-controlled fluid source adapted for applying positive fluid pressure into the sheath to push an end-effector and cause at least a first portion of the end-effector to deploy axially along a longitudinal axis of the sheath in a controlled fashion from a position within the sheath to a position beyond the distal end of the sheath, and wherein the operator-controlled fluid source is further adapted for applying negative fluid pressure into the sheath to retract at least a second portion of the end-effector into the sheath axially along the longitudinal axis of the sheath,
   wherein the end-effector moves axially relative to the operator-controlled fluid source, and wherein the relative axial movement is caused solely by the application of fluid pressure into the sheath.

2. The medical device of claim 1, wherein the end-effector comprises a first hub slidably disposed within the sheath, and adapted to move in a distal direction within the sheath in response to application of a positive fluid pressure in the sheath.

3. The medical device of claim 2, further comprising a first stop disposed within the sheath, and adapted for preventing the first hub from moving in a distal direction past the first stop.

4. The medical device of claim 3, wherein the end-effector further comprises a second hub slidably disposed within the sheath at a position distal of the first stop.

5. The medical device of claim 4, wherein the first hub includes an opening that permits a limited flow of fluid through the first hub, to apply sufficient positive fluid pressure to the second hub to move the second hub in a distal direction when the first hub is prevented from further distal movement by the first stop.

6. The medical device of claim 5, wherein the end-effector comprises a biopsy device, and wherein:
the first hub is connected to a stylet portion of the biopsy device that extends from the distal end of the sheath when the first hub is moved in a distal direction; and
the second hub is connected to a cannula portion of the biopsy device that extends from the distal end of the sheath when the second hub is moved in a distal direction.

7. The medical device of claim 6, wherein a notch is formed in the stylet portion of the biopsy device, the cannula portion of the biopsy device comprises a sharp edge, and the cannula portion of the biopsy device is adapted to slide over the stylet portion of the biopsy device when the cannula portion of the biopsy device is extended from the distal end of the sheath.

8. The medical device of claim 4, further comprising a second stop disposed within the sheath, the second stop preventing the second hub from moving in a distal direction past the second stop.

9. The medical device of claim 2, wherein the end-effector comprises a first portion and a second portion, and wherein:
the first hub is connected to the first portion of the end-effector;
an elastic member is connected to the first hub at a proximal end of the elastic member, and to the second portion of the end-effector at a distal end of the elastic member; and
the medical device further comprises a latch that holds the second portion of the end-effector in a stationary position relative to the sheath until the latch is released.

10. The medical device of claim 9, wherein the elastic member is compressed when the first hub is moved in a distal direction.

11. The medical device of claim 9, wherein the elastic member propels the second portion of the end-effector in a distal direction when the latch is released.

12. The medical device of claim 9, wherein the elastic member comprises a spring.

13. The medical device of claim 9, wherein the end-effector comprises a biopsy device, the first portion of the end-effector comprises a stylet, and the second portion of the end-effector comprises a cannula.

14. The medical device of claim 2, wherein the first hub substantially forms a seal with the sheath.

15. The medical device of claim 1, wherein the end-effector comprises a first hub slidably disposed within the sheath, and wherein applying positive fluid pressure into the sheath causes the first hub to move in a distal direction within the sheath, and applying a negative fluid pressure into the sheath causes the first hub to move in a proximal direction within the sheath.

16. The medical device of claim 15, further comprising a first stop disposed within the sheath, the first stop preventing the first hub from moving in a distal direction past the first stop.

17. The medical device of claim 16, further comprising a second stop disposed within the sheath, the second stop preventing the first hub from moving in a proximal direction past the second stop.

18. The medical device of claim 1, wherein the operator-controlled fluid source comprises a bladder permanently secured to the proximal end of the sheath, the bladder having a cavity in fluid communication with the sheath such that the cavity of the bladder and the sheath collectively store a fluid.

19. The medical device of claim 1, further comprising a handle disposed at the proximal end of the sheath.

20. The medical device of claim 19, wherein the operator-controlled fluid source is disposed on the handle.

21. The medical device of claim 20, wherein the operator-controlled fluid source comprises a bladder in fluid communication with the sheath.

22. The medical device of claim 20, wherein the operator-controlled fluid source is disposed in a position on the handle where it can be actuated by a thumb of an operator.

23. The medical device of claim 1, wherein the end-effector comprises a retrieval device.

24. The medical device of claim 23, wherein the retrieval device is selected from a basket-type retrieval device and a grasper retrieval device.

25. The medical device of claim 1, wherein the application of positive fluid pressure into the sheath results in distal movement of the end-effector relative to the sheath.

26. The medical device of claim 1, wherein the application of negative fluid pressure into the sheath results in proximal movement of the end effector relative to the sheath.

27. A medical device comprising:
a sheath having proximal and distal ends;
an end-effector slidably housed within the sheath; and
an operator-controlled fluid source configured to apply positive fluid pressure into the sheath housing the end-effector to push the end-effector and cause at least a first portion of the end-effector to move axially along a longitudinal axis of the sheath in a controlled fashion from a position within the sheath to a position beyond the distal end of the sheath, and wherein the operator-controlled fluid source is further configured to apply negative fluid pressure into the sheath to retract at least a second portion of the end-effector into the sheath axially along the longitudinal axis of the sheath,
wherein the end-effector moves axially relative to the operator-controlled fluid source, and wherein the relative axial movement is caused solely by the application of fluid pressure into the sheath.

28. The medical device of claim 27, wherein the end-effector comprises a first hub slidably disposed within the sheath, and wherein applying positive fluid pressure into the sheath causes the first hub to move in a distal direction within the sheath, and applying a negative fluid pressure into the sheath causes the first hub to move in a proximal direction within the sheath.

29. The medical device of claim 28, further comprising a first stop disposed within the sheath, the first stop preventing the first hub from moving in a distal direction past the first stop.

30. The medical device of claim 29, further comprising a second stop disposed within the sheath, the second stop preventing the first hub from moving in a proximal direction past the second stop.

31. The medical device of claim 27, wherein the fluid source is adjustable such that a level of applied positive and negative fluid pressure can be continually adjusted by an operator.

32. The medical device of claim 1, wherein the end-effector comprises a hub slidably housed within the sheath, the hub being unconnected at its proximal end to any other portion of the medical device.

33. A medical device comprising:
a sheath having proximal and distal ends;
an end-effector slidably housed within the sheath;
an operator-controlled fluid source configured to apply positive fluid pressure into the sheath housing the end-effector to push an end-effector and cause at least a first portion of the end-effector to move axially along a longitudinal axis of the sheath in a controlled fashion from a position within the sheath to a position beyond the distal end of the sheath,
wherein the operator-controlled fluid source is further configured to apply negative fluid pressure into the sheath to move the end-effector axially along the longitudinal axis of the sheath from a position beyond the distal end of the sheath to a position within the sheath; and
wherein the end-effector comprises a hub slidably housed within the sheath, wherein the hub moves axially relative to the operator-controlled fluid source, and wherein the relative axial movement is caused solely by the application of fluid pressure into the sheath.

34. The medical device of claim 1, wherein axial displacement of the end-effector between a position within the sheath to a position beyond the distal end of the sheath is controlled solely by the operator-controlled fluid source.

35. The medical device of claim 27, wherein axial displacement of the end-effector between a position within the sheath to a position beyond the distal end of the sheath is controlled solely by the operator-controlled fluid source.

36. The medical device of claim 33, further comprising a first stop disposed within the sheath, the first stop preventing the hub from moving in a distal direction past the first stop.

37. The medical device of claim 36, further comprising a second stop disposed within the sheath, the second stop preventing the hub from moving in a proximal direction past the second stop.

38. The medical device of claim 36, further comprising an elastic member, wherein a first end of the elastic member is attached to the hub and a second end of the elastic member is attached to the first stop.

39. The medical device of claim 38, wherein the elastic member is compressed during deployment.

40. The medical device of claim 20, wherein the handle is permanently secured to the proximal end of the sheath.

41. The medical device of claim 27, wherein the operator-controlled fluid source has a cavity in fluid communication with the sheath such that the cavity of the operator-controlled fluid source and the sheath, collectively, store a fluid when the end effector is positioned within the sheath and when the end-effector is positioned beyond the distal end of the sheath.

42. The medical device of claim 33, wherein the operator-controlled fluid source is configured so that a force applied to the operator-controlled fluid source in a direction perpendicular to the longitudinal axis of the sheath pressurizes a fluid stored in a cavity of the operator-controlled fluid source and the sheath, collectively, and generates a positive fluid pressure in the sheath.

* * * * *